United States Patent [19]

Martin

[11] 4,451,252
[45] May 29, 1984

[54] CANNULA

[75] Inventor: Geoffrey S. Martin, Mississauga, Canada

[73] Assignee: Vas-Cath of Canada Limited, Mississauga, Canada

[21] Appl. No.: 286,589

[22] Filed: Jul. 24, 1981

[51] Int. Cl.³ .................... A61M 5/00; A61M 25/00
[52] U.S. Cl. ........................................ 604/43; 604/164
[58] Field of Search ............ 128/214 R, 214.4, 218 R, 128/221, 347, 348, 349 R, 240, 349 B; 604/45, 43, 44, 53, 264, 280, 282–283

[56] References Cited

U.S. PATENT DOCUMENTS

| | | | |
|---|---|---|---|
| 2,175,726 | 10/1939 | Gebauer | 128/349 B |
| 4,098,275 | 7/1978 | Consalvo | 128/221 X |
| 4,134,402 | 1/1979 | Mahurkar | 128/221 X |
| 4,180,068 | 12/1979 | Jacobsen et al. | 128/214 R |
| 4,202,332 | 5/1980 | Tersteegen et al. | 128/221 X |
| 4,336,036 | 6/1982 | Leeke et al. | 128/214 R X |

FOREIGN PATENT DOCUMENTS 55-88771  7/1980  Japan .................................. 128/348

*Primary Examiner*—Dalton L. Truluck
*Assistant Examiner*—Michelle N. Lester
*Attorney, Agent, or Firm*—Gipple & Hale

[57] ABSTRACT

A dual lumen cannula particularly for use in haemodialysis by inserting the cannula into the subclavian or femoral vein of a patient to contemporaneously remove blood from the vein for treatment and to return treated blood to the vein downstream from the point of removal. The cannula includes a pair of lumens separated by a septum. Blood is withdrawn through one of the lumens and treated blood is returned through the other lumen. The cannula is formed from a flexible thermoplastic material and is sufficiently flexible to permit bending to conform to the shape of the vein without damage or kinking. The cannula has a peripheral generally cylindrical wall with a septum extending between spaced locations on the interior surface of the wall to define a pair of discrete lumens and at least one of the lumens is deformed at its end to facilitate insertion.

2 Claims, 12 Drawing Figures

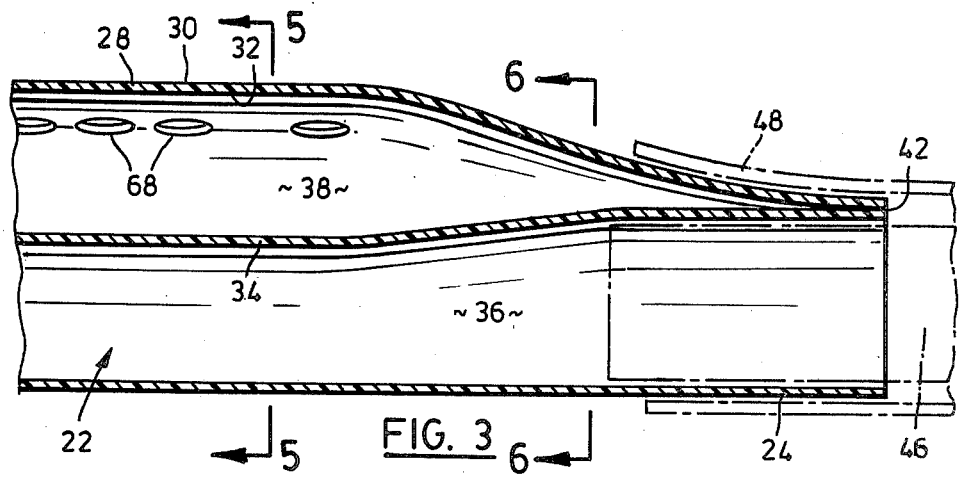
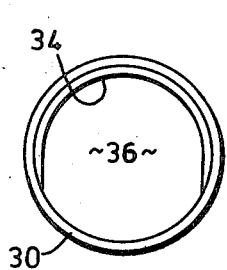
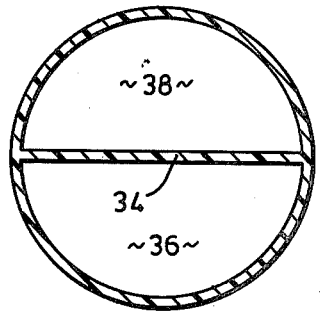
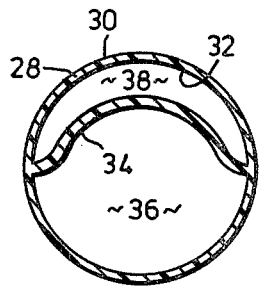
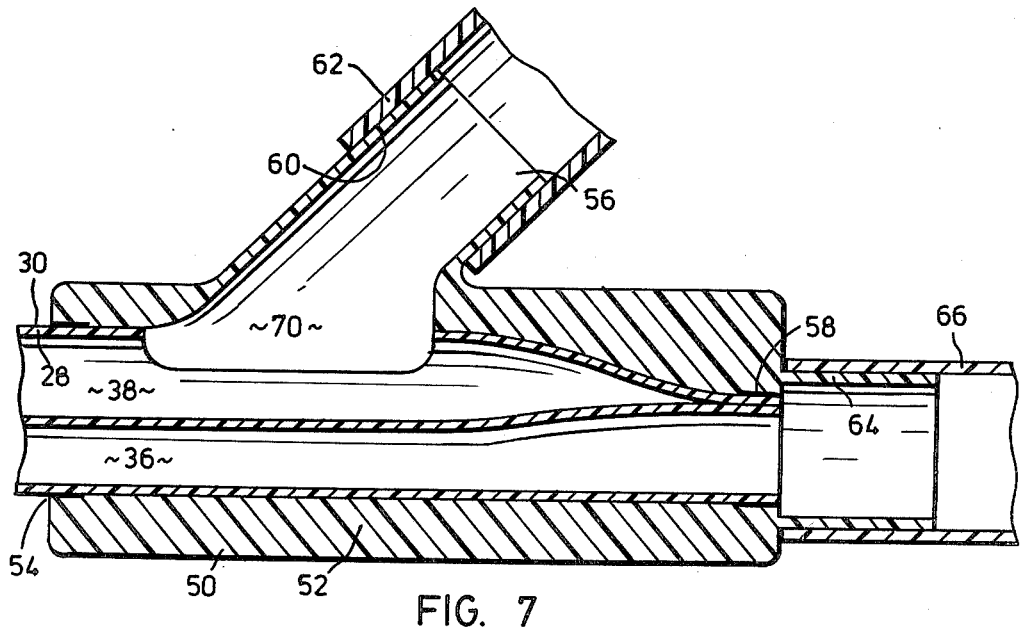

CANNULA

This invention relates to a dual lumen cannula, and more particularly to such a cannula for insertion into the subclavian or femoral veins of a patient to facilitate haemodialysis treatments.

For regular haemodialysis, permanent vascular access is normally provided by means of a surgically constructed arterio-venous fistula, created if possible in advance of need.

The conventional method of conducting haemodialysis on a patient is to introduce into an arterialized vein, normally a lower arm vein, one or two blood flow needles. Blood is removed from the patient to an exterior haemodialysis machine and then the treated blood is returned to the patient at substantially the same location. At least one puncture of the vein needs to be made for such catheter insertion whenever the patient undergoes a haemodialysis treatment. Commonly two separate needle devices are used, one for blood outflow and the other for blood return, although there is a growing interest in dual lumen catheters which have the advantage that they require only one vein puncture. Examples of conventional co-axially arranged metal cannulae for use in a limb of the patient are to be found in U.S. Pat. Nos. 4,037,599 to Raulerson; U.S. Pat. No. 4,073,297 to Koop; U.S. Pat. No. 4,134,402 to Mahurkar; and U.S. Pat. No. 4,096,860 to McLaughlin. All of these examples of prior art show a rigid, metal needle-type cannula for temporary use during the actual haemodialysis or transfusion etc. These devices are removed once the procedure is completed. None of the devices is suitable for insertion into a subclavin vein.

Although the arterio-venous fistula is the standard and accepted method for permanent vascular access, some patients experience end stage renal failure without warning, and established fistulae may fail unexpectedly. With the growth of large programmes for long-term peritoneal dialysis, an increasing number of patients must be transferred at short notice to haemodialysis because of peritonitis. Such patients do not usually have arterio-venous fistulae constructed in advance, since many of them will never need them. Patients on long-term peritoneal dialysis may also need short-term haemodialysis while they undergo abdominal surgery. Transplant recipients whose arterio-venous fistulae have thrombosed may develope acute renal failure. For all these categories of patients, the silastic teflon shunt, though immediately usable, wastes blood vessels and may not be feasible in patients whose access sites have already been used. Temporary peritoneal dialysis is not always a suitable alternative.

There is thus a need for a simple, immediately usable vascular access method which does not destroy blood vessels, and does not limit the patient's mobility. A suitable structure would incorporate the extraction and return lumens into a single cannula made from a flexible material. Whilst various proposals have been made for such cannulas, none have been entirely satisfactory, mainly because the materials that provide the necessary flexibility do not exhibit sufficient rigidity to allow insertion of the cannula.

According to the present invention there is provided a cannula having a peripheral wall defined by continuous interior and exterior surfaces and a septum extending between spaced points on said interior surface to divide said cannula into a pair of discrete lumens, one end of said cannula being stiffened for insertion into a patient by deformation of at least one of the lumens at this end.

An embodiment of the invention will now be described by way of example only with reference to the accompanying drawings in which:

FIG. 3 is a sectional side view on the line 3—3 of FIG. 2;

FIG. 4 is an end view of the cannula looking from the right of FIG. 2;

Figure 8:
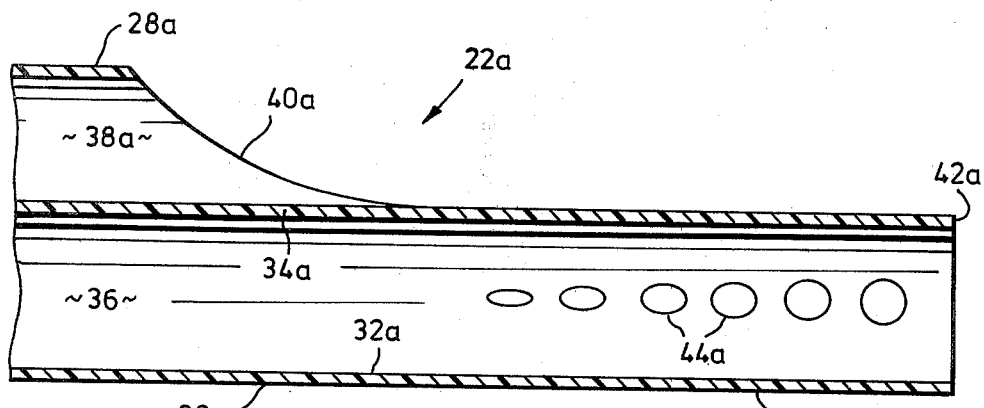
Figure 9:
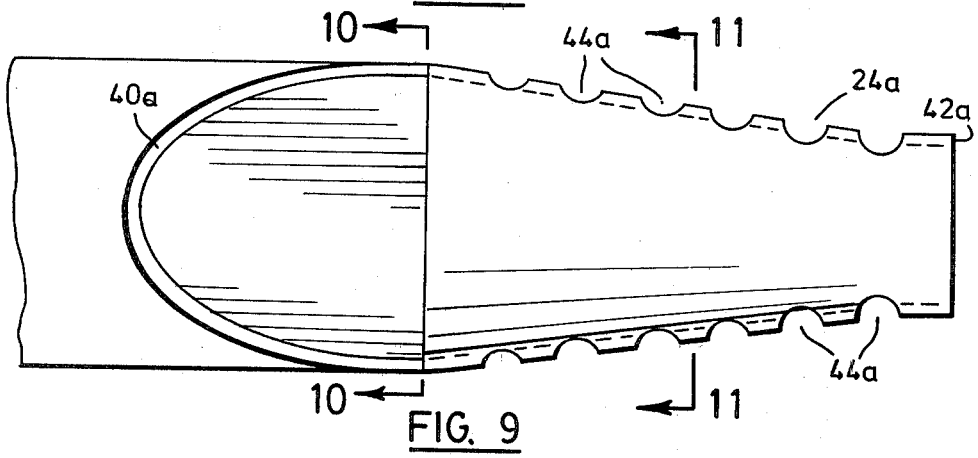
Figure 10:
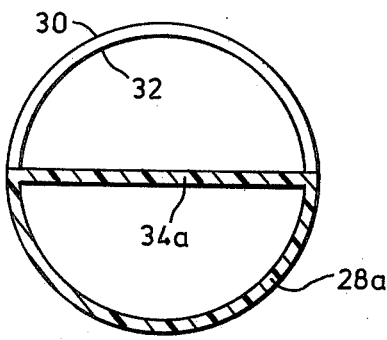
Figure 12:
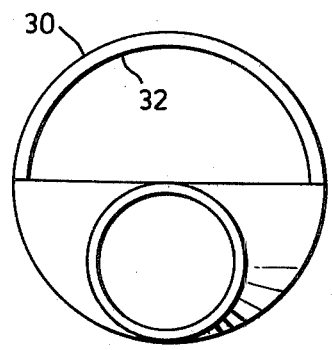
Figure 11:
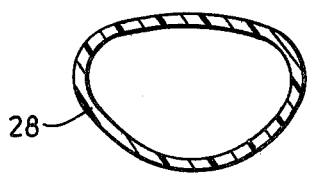

FIGS. 5 and 6 are respective sectional end views on lines 5—5 and 6—6 of FIG. 3;

FIG. 7 is a cross-sectional side view of the other end of the cannula which protrudes from the patient together with the fitting to permit attachment of external tubes to the cannula;

FIG. 8 is a view similar to FIG. 3 showing an alternative embodiment of the dual lumen cannula according to the invention;

FIG. 9 is a plan view of the cannula shown in FIG. 8;

FIGS. 10 and 11 are respective sectional end veiws on lines 10—10 and 11—11 of FIG. 9; and FIG. 12 is an end view of the cannula looking from the right of FIG. 9.

Figure 1:
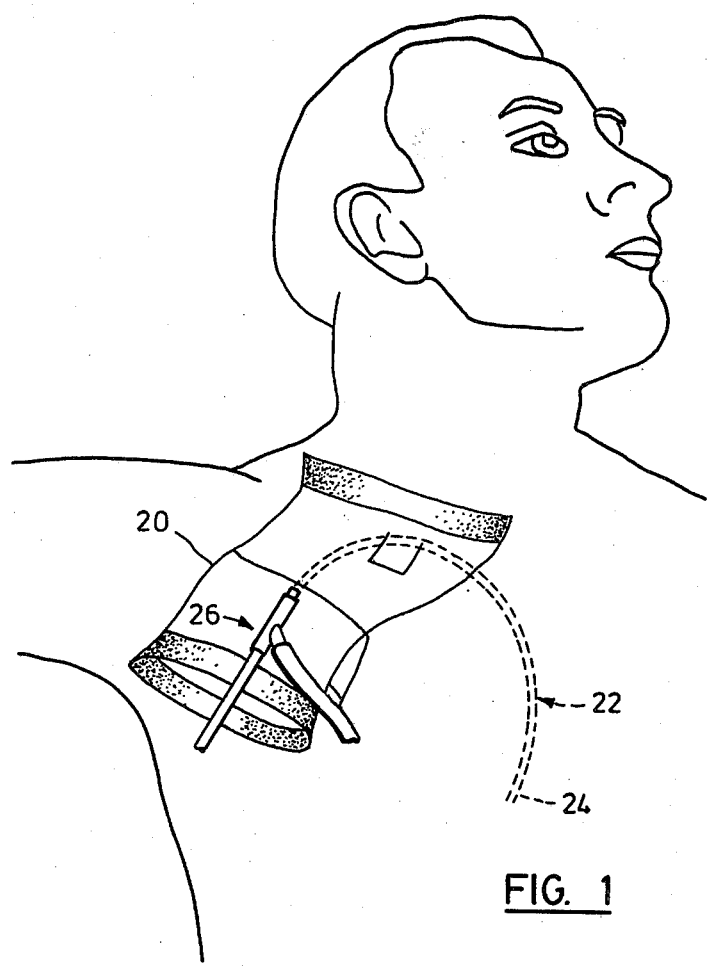
FIG. 1 is a diagrammatic view showing a dual lumen cannula inserted into a patient.
Figure 2:
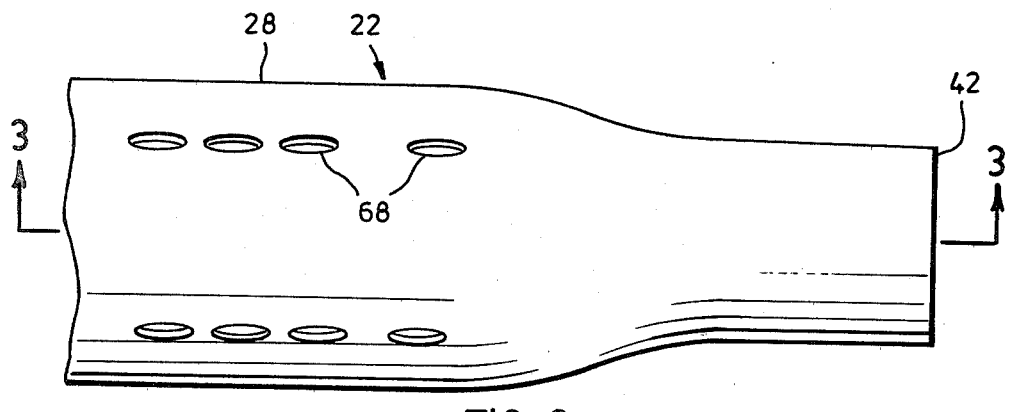
FIG. 2 is a plan view of a preferred embodiment of the end of the cannula.

Reference is first made to FIG. 1 which shows the preferred embodiment of cannula 22 used in a subclavian haemodialysis. It is shown on a patient in a mode between haemodialysis treatments. The cannula is secured in position by means of a conventional adhesive dressing 20 with the cannula 22 positioned through the dressing 20. One end 24 of the cannula 22 is introduced into the subclavian vein and the other end 26 protrudes from the patient and is secured by the dressing 20.

The one end 24 may best be seen with reference to FIGS. 2 through 6. The cannula 22 comprises a peripheral wall 28 having continuous outer and contiuous inner surfaces 30, 32 respectively. The peripheral wall 28 is generally circular in cross-section so that the main body of the cannula is cylindrical. A septum 34 extends diametrically across the interior of the cannula and is connected to the peripheral wall 28 at spaced locations. The septum therefore divides the cannula 22 in a pair of discrete lumens 36, 38 respectively. The lumen 36 serves to return blood to the vein whereas the lumen 38 serves to extract blood from the vein.

The cannula is formed from a flexible thermo-plastic material such as polyethylene, polyurethane or teflon tubing which is extruded in any conventional manner with the peripheral wall 28 and septum 34 integrally formed. As such it is inherently flexible and therefore may conform to the shape of the subclavian vein and may also be left in the patient between treatments without causing undue discomfort. However the flexible nature of the material makes feeding of the cannula difficult when initially inserted.

To overcome the above disadvantage, the end 24 of the cannula 22 is stiffened by deformation of the peripheral wall and septum adjacent the end 24.

In the preferred embodiment, shown in FIGS. 2 to 6, the septum 34 is deformed so that it merges with the inner surface 32 of the portion of the peripheral wall 28 defining the lumen 38 at the tip 42 of the end 24 of the cannula 22.

The septum 34 is deformed such that the cross-sectional area of the lumen 38 gradually decreases until it is sealed by merging of the septum 34 with the wall 28. The cross section of the lumen 36 at the tip 42 is circular but of smaller diameter than the body of the cannula 22.

This deformation is achieved by placing a mandrel indicated at 46 in chain-dot lines in FIG. 3 into the lumen 36 and by sliding a silicon rubber tube 48, also shown in chain-dot lines; over the outer surface 30 of the cannula 22. The diameter of the silicon tube is equal to the smallest outside diameter required on the finished portion of the lumen 36 and the mandrel 46 is shaped to the required internal configuration of the lumen 36. The silicon rubber is elastic and therefore will exert a peripheral force uniformally around the lumen 36. Heat is gently applied by means of a hot air gun, and passes through the silicon tubing and into the thermo-plastic material defining the wall of the cannula. The thermoplastic material melts although the silicon tubing is unaffeced by the heat. The pressure exerted by the silicon tubing then forces the melted thermo-plastic material to the shape defined by the mandrel and the excess material due to the decrease in the circumference of the lumen results in an increased thickness of the wall.

The deformed end 24 is then cooled to set the thermo-plastic material and the silicon tubing 48 and mandrel 46 removed. The gradual increase in cross-sectional area of the lumen 36 toward the tip 42 permits the mandrel 46 to be inserted and removed from the tip 42 of the cannula 22.

A plurality of holes 68 are formed in the peripheral wall 28 of the lumen 38 to allow blood to blow from the vein into the lumen 38. The passageway defined by these holes is therefore located upstream from the tip 42 of lumen 36 which acts as an exit passageway for the return flow of blood into the vein.

As seen in FIG. 7, the outer end of the cannula is provided with a fitting 50 which enables the two discrete blood flows to be transferred to a treatment machine. The fitting 50 comprises a chamber 52 with an inlet port 54 and a pair of outlet ports 56, 58 respectively. The inlet port 54 is dimensioned to be a snug fit on the outer surface 30 of the cannula 22 so that a seal is provided between the fitting and the cannula. The outlet port 56 communicates with the interior of the chamber 52 and provides a stub 60 to which a flexible tube 62 may be attached. A similar stub 64 is provided adjacent the outlet port 58 to receive a second length of flexible tubing 66. A portion of the peripheral wall 28 surrounding the lumen 38 is removed, as indicated at 70, to provide a passageway for blood in the lumen 38 to flow out of the outlet port 56. The end of the cannula 38 is sealed by deformation of the septum 34 in a manner similar to that described above by means of a mandrel and silicon so that a single circular opening of reduced diameter is provided for the lumen 36. The outlet port 58 is dimensioned to be a snug fit around the finished diameter of the lumen 36 so that blood flowing from the apparatus back through the lumen 36 is maintained separate from blood being removed through the lumen 38 and the tube 62. The fitting 50 may be made through the lumen 38 and the tube 62 and is of any suitable plastic material formed by injection molding. In addition a deformation of the end 26 of the cannula increases its stiffness to assist in insertion of the tube in the fitting 50. If preferred, the outlet port 50 may be formed with a nipple extending into the chamber 52 so that the lumen 36 fits over the nipple to provide a seal.

It will be seen therefore that a flexible cannula is provided with a pair of discrete lumens to remove and replace blood from the vein. The deformation of the end of the cannula increases its stiffness to facilitate insertion into the vein with rendering the body of the cannula inflexible.

An alternative embodiment of the end of the cannula is shown in FIGS. 8–12. Similar reference numerals are used to indicate components equivalent to those described with reference to FIGS. 2–6 with a suffix 'a' added for clarity of description.

In this embodiment, the end 24a is formed by removing the portion of the peripheral wall 28a defining the lumen 38a. The peripheral wall is cut to define a curved end surface 40a for the lumen 38a and to merge smoothly with the septum 34a at the intersection of the septum 34a with the inner surface 32a. The septum 34a is then deformed to provide a circular cross-section at the tip 42a of the lumen 36a. The deformation of the septum and the portion of the peripheral wall defining the lumen 36a results in a gradual increase in the thickness of the peripheral wall 28a as the tip 42a is approached. The increased wall thickness therefore stiffens the tip 42a and facilitates insertion of the cannula.

As can best be seen in FIGS. 9–12, the cross-section of the lumens 36a, 38a is initially semi-circular at the point at which the lumen 38a and smoothly tapers to provide a circular cross-section at the tip 42a of the lumen 36a.

Because of the reduction in the diameter of the extreme end 42a of the lumen 38a a plurality of holes 44a are formed in the peripheral wall 28a to increase the cross-section of the lumen for blood to flow out. Once again, the deformation of the wall 28a to provide an increased thickness at the tip 42a results in the required stiffness of the end 24a of the cannula 22a. In this embodiment however the mandrel 46a must be inserted from the other end 26a of the cannula 22a because of the gradual reduction in cross-section toward the tip 42a. The end 26a of the cannula 22a may be formed as shown in FIG. 7 after the mandrel 46a has been removed.

Although the cannula has been described in use in a subclavian vein, it can also be used in a femoral vein. It will be evident that to facilitate such insertion a needle can be entered into the lumen 36 (FIG. 7) and out the other end of the cannula shown in FIG. 3. After insertion the needle is withdrawn in the usual way having the cannula in place. Similarly, the cannula can be used at other locations for other purposes.

I claim:

1. A flexible cannula for providing two discrete flows of blood when in position, the cannula comprising: an elongate portion having an outer wall and an integral septum extending between two locations on the outer wall to divide the portion into first and second lumens of similar cross-section; means coupled to the lumens at a first end of the elongate portion to provide flow into the first lumen and to receive flow from the second lumen; a first portion adjacent the other end of the elongate portion providing flow out of the free end of the first lumen at an end portion thereof and a second portion adjacent the other end of the elongate portion to enable flow into the free end of said second lumen displaced along the longitudinal axis of the cannula toward the first end, the first portion being rounded and formed by deforming the septum into a generally semi-cylindrical shape and deforming a part of the outer wall into a complementary semi-cylindrical shape into sealing engagement with the septum to complete the rounded shape of the end portion of the first lumen, said rounded shape having a circumference less than the circumference of the cannula in the elongate portion and having at least part of its peripheral wall increased in thickness around the circumference to rigidify the end portion so that deformation of the first lumen is minimized during insertion of the end portion into a blood vessel.

2. A flexible cannula as claimed in claim 1 in which the second lumen is terminated at said second end by deforming the outer wall of the second lumen into sealing engagement with the septum and in which said second portion has at least one opening provided in the outer wall to provide flow into this lumen.

* * * * *